(12) United States Patent
Takada

(10) Patent No.: US 7,698,944 B2
(45) Date of Patent: Apr. 20, 2010

(54) ULTRASONIC METHOD AND APPARATUS FOR EVALUATING SPOT WELD ZONE

(75) Inventor: Hajime Takada, Kawasaki (JP)

(73) Assignee: JFE Steel Corporation (JP)

( * ) Notice: Subject to any disclaimer, the term of this patent is extended or adjusted under 35 U.S.C. 154(b) by 249 days.

(21) Appl. No.: 11/661,741

(22) PCT Filed: Aug. 31, 2005

(86) PCT No.: PCT/JP2005/016369

§ 371 (c)(1),
(2), (4) Date: Mar. 1, 2007

(87) PCT Pub. No.: WO2006/025591

PCT Pub. Date: Mar. 9, 2006

(65) Prior Publication Data

US 2007/0240512 A1      Oct. 18, 2007

(30) Foreign Application Priority Data

Sep. 1, 2004    (JP)    .............................. 2004-254477

(51) Int. Cl.
    *G01N 29/04* (2006.01)
(52) U.S. Cl. .............................. 73/588; 73/626; 73/641; 73/644
(58) Field of Classification Search .................. 73/588, 73/626, 628, 632, 634, 641, 644; 219/109, 219/110; 228/104; 600/443, 447
    See application file for complete search history.

(56) References Cited

U.S. PATENT DOCUMENTS

| | | | | |
|---|---|---|---|---|
| 3,115,770 A | * | 12/1963 | Cram et al. | .................... 73/600 |
| 3,302,453 A | * | 2/1967 | Wood et al. | .................... 73/622 |
| 3,893,223 A | * | 7/1975 | Mims | ....................... 228/110.1 |
| 4,210,028 A | * | 7/1980 | Hildebrand | .................... 73/598 |
| 4,375,165 A | * | 3/1983 | de Sterke | ..................... 73/622 |
| 5,170,929 A | * | 12/1992 | Long et al. | .................... 228/102 |
| 5,652,389 A | * | 7/1997 | Schaps et al. | ................. 73/643 |
| 6,072,144 A | * | 6/2000 | Perryman | ................... 219/109 |
| 6,279,399 B1 | * | 8/2001 | Holm | ......................... 73/626 |
| 6,295,025 B1 | * | 9/2001 | Smith | ........................ 342/360 |

(Continued)

FOREIGN PATENT DOCUMENTS

JP       62-52456 A       3/1987

(Continued)

*Primary Examiner*—J M Saint Surin
(74) *Attorney, Agent, or Firm*—DLA Piper LLP (US)

(57) ABSTRACT

Even in measurement in which the measurement time is limited to a short time, soundness of a spot weld zone can be evaluated with high reliability without being influenced by a positional deviation between an ultrasonic probe and the spot weld zone and the coupling condition between an ultrasonic probe and a metal sheet. Specifically, ultrasonic waves propagating along the surface of a test object are transmitted in a plurality of directions from a plurality of wave sending positions outside the spot weld zone in metal sheets (1a, 1b), and ultrasonic waves propagating along the surface of the test object with propagation paths not including the spot weld zone and ultrasonic waves propagating along the surface of the test object with propagation paths including the spot weld zone are received at a plurality of wave receiving positions outside the spot weld zone to evaluate the soundness of the spot weld zone.

15 Claims, 12 Drawing Sheets

U.S. PATENT DOCUMENTS

| | | | |
|---|---|---|---|
| 6,414,260 B1 * | 7/2002 | Vogt | 219/109 |
| 6,546,803 B1 * | 4/2003 | Ptchelintsev et al. | 73/632 |
| 7,335,160 B2 * | 2/2008 | Satoh | 600/437 |
| 7,448,272 B2 * | 11/2008 | Aznar et al. | 73/634 |
| 2004/0245315 A1 * | 12/2004 | Maev et al. | 228/8 |
| 2005/0230360 A1 * | 10/2005 | Maev et al. | 219/109 |

FOREIGN PATENT DOCUMENTS

| | | |
|---|---|---|
| JP | 6-265529 A | 9/1994 |
| JP | 11-2627 A | 1/1999 |
| JP | 2000-146928 A | 5/2000 |
| JP | 2002-131297 A | 5/2002 |
| JP | 2002-207028 A | 7/2002 |
| JP | 2003-279546 A | 10/2003 |
| JP | 2004-163210 A | 6/2004 |
| WO | WO 86/04416 A1 | 7/1986 |

* cited by examiner

US 7,698,944 B2

ULTRASONIC METHOD AND APPARATUS FOR EVALUATING SPOT WELD ZONE

RELATED APPLICATION

This is a §371 of International Application No. PCT/JP2005/016369, with an international filing date of Aug. 31, 2005 (WO 2006/025591 A1, published Mar. 9, 2006), which is based on Japanese Patent Application No. 2004-254477, filed Sep. 1, 2004.

TECHNICAL FIELD

The technology in this disclosure relates to a method and apparatus for ultrasonic nondestructive inspection of a diameter and soundness of a welded metal portion (also referred to as a "weld solidified structure" or a "nugget" hereinafter) formed by spot welding.

BACKGROUND ART

For example, in plants for manufacturing automobile bodies, a spot weld inspection method which can be easily carried out has been recently desired for inspecting spot weld zones with high efficiency on site.

Since an automobile body is assembled by spot welding at thousands of points, quality of spot welding directly influences the strength and durability of the body, and thus it is very important to inspect whether or not spot welding is properly performed. As a method of inspecting spot weld zones, chisel inspection has been carried out for deciding the quality by confirming whether or not a spot weld zone is separated by a cold chisel inserted between spot-welded metal sheets. However, in the chisel inspection, spot weld zones may be broken, and thus it is difficult to precisely determine the quality of spot welding by the chisel inspection. Also, members each having a spot weld zone broken by the chisel inspection cannot be used for products, and there is thus the problem of increasing the cost.

Therefore, various apparatuses and methods have been recently proposed for ultrasonic nondestructive inspection of the quality of spot welding.

For example, Japanese Unexamined Patent Application Publication Nos. 2000-146928, 2002-131297, 11-2627, and 6-265529 disclose methods and apparatuses in each of which an ultrasonic wave is vertically incident onto a sheet surface to detect a reflected wave, for evaluating the quality of a spot weld zone formed by welding two stacked sheets. Japanese Unexamined Patent Application Publication No. 62-52456 discloses an ultrasonic flaw detector based on local immersion method in which a pair of immersion probes disposed on and below a test piece to be opposed to each other with the test object disposed therebetween, and the test object is horizontally moved so that a spot weld zone of the test object is scanned by an ultrasonic beam transmitted from the transmitting probe and the presence of a flaw in the spot weld zone is determined on the basis of a signal received by the receiving probe.

In the above-mentioned prior art, an ultrasonic wave is sent and received vertically to the plate-shaped test object. Therefore, in an inclined surface 102 formed around each dimple 102b formed in a spot weld zone 102 of a test object illustrated in FIG. 10, an ultrasonic beam cannot be efficiently incident onto the test object. There is thus the problem of difficulty in precisely detecting the size of a nugget 102a formed in the spot weld zone 102.

In other words, as shown in FIG. 10, when an upper sheet 101a and a lower sheet 101b are stacked and welded together by spot welding, a weld solidified structure 102a referred to as a "nugget" is formed in the spot weld zone 102 at a joint between the upper and lower sheets 101a and 101b. In spot welding, the upper and lower sheets 101a and 101b are strongly pressed by electrode tips not shown in the drawing to form the dimples 102b corresponding to the shapes of the electrode tips in the surfaces of the upper and lower sheets 101a and 101b.

Furthermore, the conical inclined surfaces 102c are formed between the bottoms of the dimples 102b and the surfaces of the upper and lower sheets 101a and 101b. In normal welding, the diameter of the nugget 102a is slightly larger than or substantially the same as the diameter of the electrode tips used for welding. Since the electrode tips have a chamfered cylindrical tip shape, the inner diameter of the dimples 102b is slightly smaller than the diameter of the cylindrical portions of the electrode tips. Therefore, the inner diameter of the dimples 102b is generally slightly smaller than the diameter of the nugget 102a. In abnormal welding, the diameter of the nugget is smaller than that in normal welding, thereby causing abnormality such as lack of strength. In FIG. 10, symbol S represents the toe of the nugget 102a. The toe refers to a point of intersection between the front or back surface of the upper sheet 101a or the lower sheet 101b and the boundary of a weld metal.

As described above, in the spot weld zone 102, the conical inclined surfaces 102c are formed between the bottoms of the respective dimples 102b and the surfaces of the upper and lower sheets 101a and 101b. Therefore, an ultrasonic wave is reflected by the inclined surfaces 102c and little transmitted into the test object, thereby obtaining substantially no signal from a portion to be inspected by use of an ultrasonic inspection apparatus of the prior art in which an ultrasonic beam is sent and received vertically to the surfaces of the upper and lower sheets 101a and 101b of a test object. As described above, the size of the nugget 102a is slightly larger than or substantially the same as the diameter of the electrode tips, and thus the toe S of the nugget 102a substantially overlaps the inclined surfaces 102c formed in the test object. Therefore, as an ultrasonic wave is reflected by one of the inclined surfaces 102c, a correct signal cannot be obtained from a portion near the nugget toe S, thereby causing difficulty in precisely determining the nugget diameter and deciding whether or not a defect such as a crack or the like is present.

In Japanese Unexamined Patent Application Publication No. 2004-163210, the inventor of the present invention has already proposed an ultrasonic method of evaluating a spot weld zone formed by welding a plurality of stacked metal sheets, in which a Lamb wave is excited in the metal sheets outside the spot weld zone toward a weld metal, and the Lamb wave is transmitted through the weld metal and then received after the transmission to evaluate soundness of the spot weld zone. In this method, evaluation of the spot weld zone was succeeded without being influenced by the inclined surfaces formed around the dimples formed in the spot weld zone. However, in Japanese Unexamined Patent Application Publication No. 2004-163210, it was found that a deviation of the positional relation between the two Lamb wave probes and the spot weld zone from a predetermined positional relation, which may happen in disposing two Lamb wave probes opposite to each other with the spot weld zone disposed therebetween, causes a deviation of the Lamb wave propagation path from the center of the spot weld zone, thereby failing to correctly evaluate the soundness of the spot weld zone. This problem significantly occurs when the relative positional relation between the Lamb wave probes and the spot weld zone cannot be sufficiently controlled because the measurement time is limited to a short time.

The Lamb wave is also referred to as a "plate wave" and is produced by oblique incidence of an ultrasonic wave onto a thin plate (a metal sheet or a non-metal sheet) at a specified angle of incidence. Obliquely traveling longitudinal and transverse waves generated in a thin plate from oblique incidence refraction propagate and interfere with each other while repeating reflection followed by mode conversion at the front and back surfaces of the thin plate, thereby producing a traveling wave displaced symmetrically or asymmetrically with respect to the center of the thin plate in the thickness direction. This traveling wave is the Lamb wave (refer to Joseph L. Rose, Ultrasonic waves in solid media, pp. 101-126, Cambridge Univ. Press, Cambridge, 1999). A Lamb wave probe is an ultrasonic probe for making an ultrasonic wave incident on a thin plate at a specified angle of incidence in order to excite a Lamb wave in the thin plate. The Lamb wave probe can also be used for receiving Lamb waves.

It was further found that in evaluating the soundness of a spot weld zone using the method disclosed in Japanese Unexamined Patent Application Publication No. 2004-163210, the soundness of a spot weld zone cannot be precisely evaluated in some cases because the amplitude of a transmitted Lamb wave may be changed depending on a change in the coupling condition between two Lamb wave probes and a metal sheet unless a method of detecting the amplitudes $A_1$ and $A_2$ of transmitted Lamb waves at two frequencies $f_1$ and $f_2$ ($f_1 < f_2$) shown in claim 3 of Japanese Unexamined Patent Application Publication No. 2004-163210 and determining the ratio ($A_2/A_1$) is used. This problem significantly occurs when the coupling condition between two Lamb wave probes and a metal sheet cannot be sufficiently stabilized because the measurement time is limited to a short time. In order to use Lamb waves at two frequencies, it is necessary to arrange two piezoelectric elements in a line in a Lamb wave probe because of the need for the Lamb waves to have the same passage path. Therefore, a Lamb wave probe is inevitably increased in size, thereby causing the problem of difficulty in evaluating a spot weld zone in a narrow portion.

It could therefore be advantageous to evaluate the soundness (the presence of a nugget, the nugget diameter, and weld cracking) of a spot weld zone with high reliability within a short measurement time (for example, 5 seconds or less per spot) without the influence of a deviation between the positions of an ultrasonic probe and the spot weld zone and a coupling condition between an ultrasonic probe and a metal sheet.

SUMMARY

I provide an ultrasonic method for evaluating a spot weld zone formed by welding two or more stacked metal sheets, wherein provided that an ultrasonic wave propagating in a sectional plane which has one axis parallel to the surface of the metal sheets or the spot weld zone and has the other axis parallel to the thickness direction is referred to as an ultrasonic wave propagating along the surface of a test object, ultrasonic waves propagating along the surface of a test object are transmitted in a plurality of directions from a plurality of wave sending positions outside the spot weld zone in the metal sheets, and ultrasonic waves propagating along the surface of the test object with propagation paths not including the spot weld zone and ultrasonic waves propagating along the surface of the test object with propagation paths including the spot weld zone are received at a plurality of wave receiving positions outside the spot weld zone to evaluate the soundness of the spot weld zone on the basis of the ultrasonic waves received at the plurality of wave receiving positions.

The amplitudes of the received ultrasonic waves (also referred to as the "heights of transmitted waves") are detected to measure the diameter of a nugget of the spot weld zone.

I also provide an ultrasonic apparatus for evaluating a spot weld zone formed by welding two or more stacked metal sheets, wherein provided that an ultrasonic wave propagating in a sectional plane which has one axis parallel to the surface of the metal sheets or the spot weld zone and has the other axis parallel to the thickness direction is referred to as an ultrasonic wave propagating along the surface of a test object, the apparatus includes means for transmitting ultrasonic waves propagating along the surface of a test object in a plurality of directions from a plurality of wave sending positions outside the spot weld zone in the metal sheets, means for receiving ultrasonic waves propagating along the surface of the test object with propagation paths not including the spot weld zone and ultrasonic waves propagating along the surface of the test object with propagation paths including the spot weld zone at a plurality of wave receiving positions outside the spot weld zone, and means for evaluating the soundness of the spot weld zone on the basis of the ultrasonic waves received at the plurality of wave receiving positions.

The amplitudes of the received ultrasonic waves are detected to measure the diameter of a nugget of the spot weld zone.

The apparatus further includes display means for displaying the amplitudes of the signals transmitted from the respective wave sending positions and received at the respective wave receiving positions in a two-dimensional matrix in which the wave sending positions are related to the respective wave receiving positions.

The positional relation between the spot weld zone and the means for transmitting ultrasonic waves and the means for receiving ultrasonic waves is aligned on the basis of the display results of the display means so that the influence of a positional deviation between an ultrasonic probe and the spot weld zone can be removed to permit the high-reliability evaluation of soundness.

The amplification gains of signals of the received ultrasonic waves are controlled on the basis of the amplitudes of the ultrasonic waves propagating along the surface of the test object with the propagation paths not including the spot weld zone so that the influence of a coupling condition between ultrasonic probes and the metal sheets can be removed to permit the high-reliability evaluation of soundness.

The means for transmitting ultrasonic waves propagating along the surface of a test object in a plurality of directions from a plurality of wave sending positions includes an ultrasonic probe provided with a piezoelectric element array.

The means for receiving ultrasonic waves at a plurality of wave receiving positions includes an ultrasonic probe provided with a piezoelectric element array.

Furthermore, a flexibly deformable member is attached to the contact surface of the ultrasonic probe provided with the piezoelectric element array.

Figure 1:
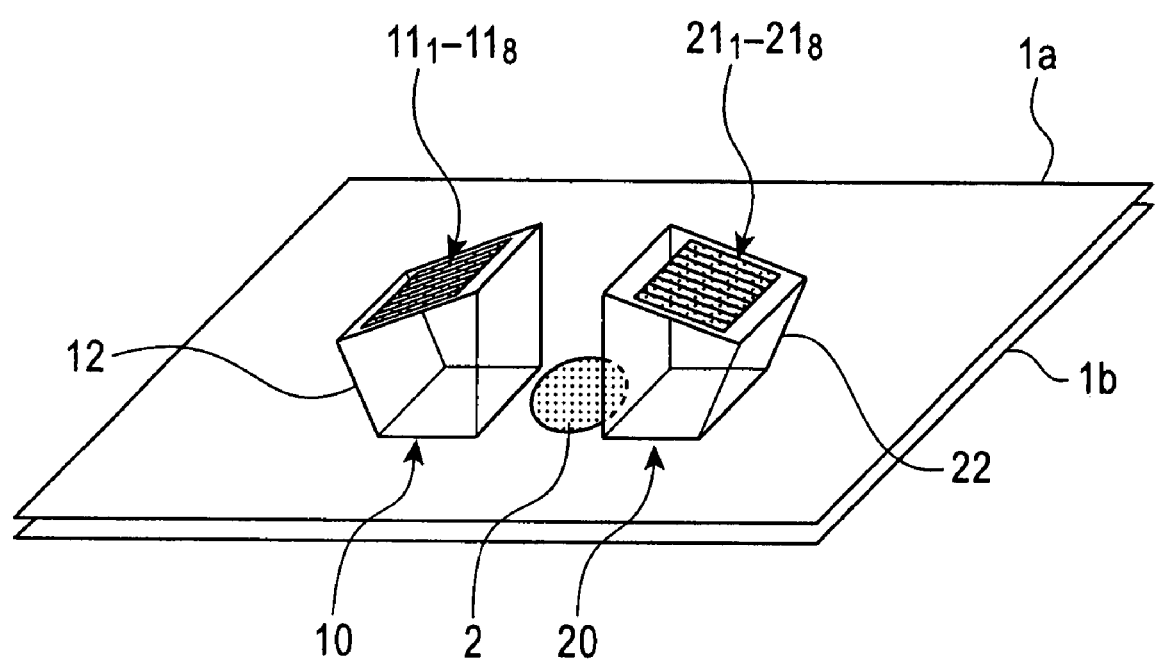
FIG. 1 is a perspective view showing a constitution according to one selected embodiment.

REFERENCE NUMERALS 1a, 101a upper sheet
1b, 101b lower sheet
2, 102 spot weld zone
2a, 102a nugget
2b weld solidified structure (weld metal)
10, 20 ultrasonic probe
11, 21 piezoelectric element array
12, 22 resin wedge For example, as the coupling medium, glycerin, glycerin paste, machine oil, alcohol, or water can be used.

Figure 2:
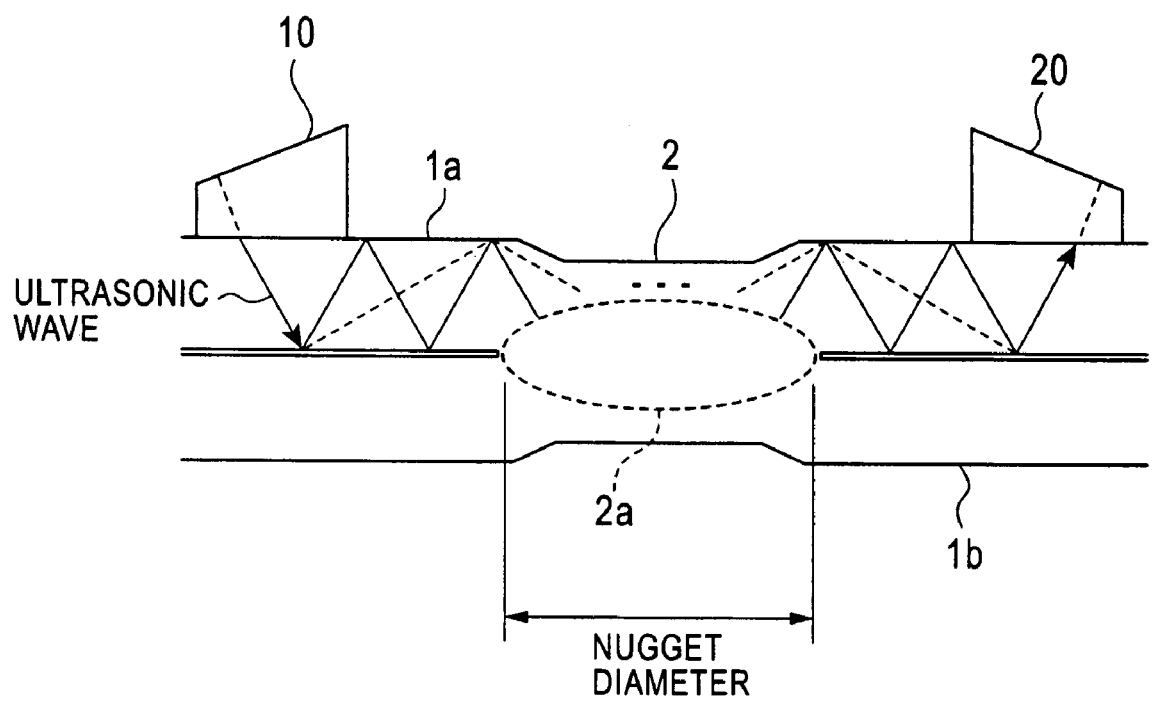
FIG. 2 is a sectional view showing an ultrasonic wave propagation path to help explain the operating principle.

In addition, ultrasonic waves are transmitted to the upper sheet 1a from a plurality of positions using the ultrasonic probe 10 provided with the piezoelectric element array 11. The ultrasonic probe 10 has a structure in which the piezoelectric element array 11 is attached to a resin wedge 12. Each of the ultrasonic waves transmitted from the piezoelectric element array 11 reach obliquely onto the upper sheet 1a. As shown in FIG. 2, as a result of the oblique incidence of an ultrasonic wave, an obliquely traveling ultrasonic wave with respect to the surface of the upper sheet 1a is transmitted in the upper sheet 1a. The obliquely traveling ultrasonic wave includes a longitudinal wave and a transverse wave and propagates in the upper sheet 1a while repeating reflection accompanied by mode conversion at the bottom and at the surface of the upper sheet 1a. In FIG. 2, the transverse wave is shown by a solid line, and the longitudinal wave is shown by a broken line. When the angle of incidence of an ultrasonic wave on the upper sheet 1a is an appropriate value, an ultrasonic wave propagating while repeating the reflection becomes a wave called "a Lamb wave". The propagating ultrasonic wave is received by the ultrasonic probe 20 provided with the piezoelectric element array 21. The ultrasonic probe 20 has a structure in which the piezoelectric element array 21 is attached to a resin wedge 22. As the resin wedges 12 and 22, a polystyrol (polystyrene) resin, an acrylic resin, or a polyimide resin can be used. When a polystyrol (polystyrene) resin and glycerin paste are used as the resin wedges 12 and 22 and the coupling medium, respectively, the influence of the surface roughness and curvature of the metal sheets on ultrasonic transmission between an ultrasonic probe and a test object can be minimized. Therefore, this combination is preferred.

For example, as the coupling medium, glycerin, glycerin paste, machine oil, alcohol, or water can be used.

In addition, ultrasonic waves are transmitted to the upper sheet 1a from a plurality of positions using the ultrasonic probe 10 provided with the piezoelectric element array 11. The ultrasonic probe 10 has a structure in which the piezoelectric element array 11 is attached to a resin wedge 12. Each of the ultrasonic waves transmitted from the piezoelectric element array 11 reach obliquely onto the upper sheet 1a. As shown in FIG. 2, as a result of the oblique incidence of an ultrasonic wave, an obliquely traveling ultrasonic wave with respect to the surface of the upper sheet 1a is transmitted in the upper sheet 1a. The obliquely traveling ultrasonic wave includes a longitudinal wave and a transverse wave and propagates in the upper sheet 1a while repeating reflection accompanied by mode conversion at the bottom and at the surface of the upper sheet 1a. In FIG. 2, the transverse wave is shown by a solid line, and the longitudinal wave is shown by a broken line. When the angle of incidence of an ultrasonic wave on the upper sheet 1a is an appropriate value, an ultrasonic wave propagating while repeating the reflection becomes a wave called "a Lamb wave". The propagating ultrasonic wave is received by the ultrasonic probe 20 provided with the piezoelectric element array 21. The ultrasonic probe 20 has a structure in which the piezoelectric element array 21 is attached to a resin wedge 22. As the resin wedges 12 and 22, a polystyrol (polystyrene) resin, an acrylic resin, or a polyimide resin can be used. When a polystyrol (polystyrene) resin and glycerin paste are used as the resin wedges 12 and 22 and the coupling medium, respectively, the influence of the surface roughness and curvature of the metal sheets on ultrasonic transmission between an ultrasonic probe and a test object can be minimized. Therefore, this combination is preferred.

Furthermore, gentle unevenness may be formed in the surface of a metal sheet around a spot weld zone of an automobile or the like. In this case, when a flexibly deformable member of rubber or the like is attached to the contact surface between each of the ultrasonic probes 10 and 20 and the test object, coupling between each of the ultrasonic probes 10 and 20 and the metal sheet surface is easily stabilized, thereby causing a practical effect. As the flexibly deformable member, a soft member with an international rubber hardness IRHD of 30 or less based on ISO 48:1994 is preferred. Examples of such a member include silicone rubber, natural rubber, and ethylene-propylene rubber.

Figure 3:
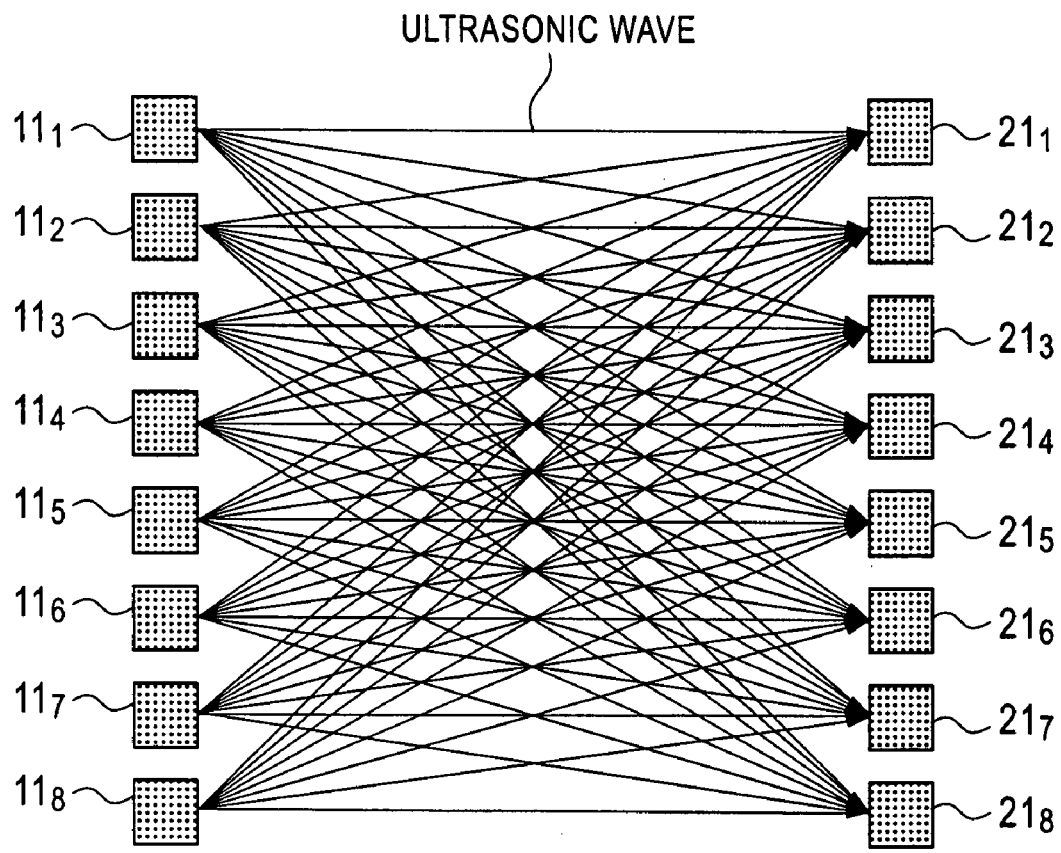
FIG. 3 is a plan view showing ultrasonic wave propagation paths to help explain the operating principle.

By using the ultrasonic probe 10 provided with the piezoelectric element array 11 and the ultrasonic probe 20 provided with the piezoelectric element array 21, ultrasonic waves propagating in the planar paths (paths in a top view of the metal sheets) shown in FIG. 3 can be received. The respective piezoelectric elements in the piezoelectric element array 11 of the ultrasonic probe 10 are represented by $11_1$ to $11_N$, and the respective piezoelectric elements in the piezoelectric element array 21 of the ultrasonic probe 20 are represented by $21_1$ to $21_N$. For example, N is 4 to 256. N may not be an even number and N of receiving piezoelectric elements need not be the same as N of sending piezoelectric elements. In FIG. 3, N is 8. Since ultrasonic waves transmitted from the piezoelectric elements $11_1$ to $11_N$ in the piezoelectric element array have spatial divergence (For example, assuming that the dimension of each piezoelectric element in the array direction is 1.5 mm, and the nominal frequency of each piezoelectric element is 5 MHz, the divergence of ultrasonic waves represented by a beam angle of divergence between first zero pressure points is 24 to 45° in a plane parallel to the metal sheet surface. This value varies depending on the propagation mode of ultrasonic waves used in measurement.), ultrasonic waves can be transmitted along the planar paths shown in FIG. 3 from the probes $11_1$ to $11_N$.

The ultrasonic wave transmitted from the piezoelectric element $11_1$ of the ultrasonic probe 10 is received by the piezoelectric elements $21_1$ to $21_N$ of the ultrasonic probe 20. Next, the ultrasonic wave transmitted from the piezoelectric element $11_2$ of the ultrasonic probe 10 is received by the piezoelectric element $21_1$ to $21_N$ of the ultrasonic probe 20. This process is performed by sequentially changing the piezoelectric element $11_n$(n=1, 2, . . . , N) for wave transmission until the ultrasonic waves transmitted from the piezoelectric element $11_N$ of the ultrasonic probe 10 are received by the piezoelectric elements $21_1$ to $21_N$ of the ultrasonic probe 20. As a result, ultrasonic waves transmitted from a plurality of positions and propagating in a plurality of directions can be received by the piezoelectric element $21_1$ to $21_N$ of the ultrasonic probe 20.

Figure 4:
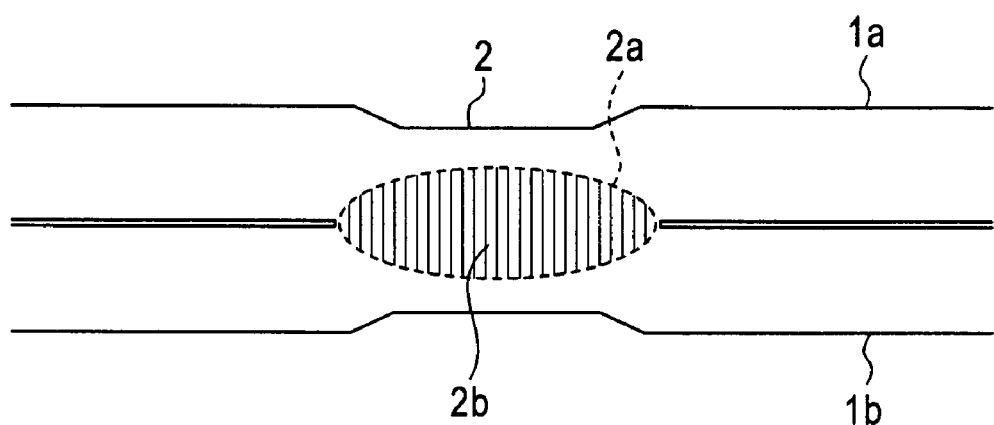
FIG. 4 is a sectional view showing a spot weld zone.

As shown in FIG. 4, the nugget 2a formed in the spot weld zone 2 has a weld solidified structure 2b having directivity substantially parallel to the thickness direction (vertical to the rolling direction of the sheets). The weld solidified structure 2b corresponds to a weld metal of this disclosure. In addition, the weld solidified structure 2b is referred to as a "dendrite structure", and includes a collection of coarse crystals extending in one direction. Therefore, the weld solidified structure 2b has a property of low transmission of ultrasonic waves (large attenuation) as compared with a metal structure of a steel sheet. Thus, ultrasonic waves propagating along the surface of the test object are attenuated depending on the length (also referred to as the "nugget diameter") of the weld solidified structure 2b parallel to the sheet surface. As a result, when the paths of the ultrasonic waves include the weld solidified structure 2b, the ultrasonic waves propagating along the paths shown in FIG. 3 are attenuated according to the length of the weld solidified structure 2b present in the paths and then received by the ultrasonic probe 20.

Although my disclosure is applied to a weld inspection of metal sheets, such application is not limited to this. Also, the number of metal sheets to be welded is not limited to 2, and when the number is 3, 4, or 5, the same measurement as with the number of 2 can be performed.

The ultrasonic waves propagating along the surface of the test object may be any of Lamb waves (for example, $A_0$ mode, $S_0$ mode, $A_0S_0$ mode, $A_2$ mode, or $S_2$ mode, for details, refer to Joseph L. Rose, Ultrasonic waves in solid media, pp. 101-126, Cambridge Univ. Press, Cambridge, 1999), longitudinal waves, transverse waves, or a mixture of longitudinal and transverse waves.

When the whole width of each of the piezoelectric element array $11_1$ to $11_N$ and the piezoelectric element array $21_1$ to $21_N$ in the array direction is 1.1 to 2.0 times the maximum of the nugget diameter to be measured, the positional relation between the spot weld zone and the piezoelectric element arrays is controlled so that the spot weld zone is near the center of piezoelectric element array in the array direction. In this case, ultrasonic waves propagating along the surface of the test object with the propagation paths not including the spot weld zone and ultrasonic waves propagating along the surface of the test object with the propagation paths including the spot weld zone can be received.

Furthermore, by making the piezoelectric element size in the array direction smaller, the measurement accuracy can be increased. In this connection, the number N of the piezoelectric elements in the piezoelectric element arrays $11_1$ to $11_N$ and $21_1$ to $21_N$ increases. The number of the piezoelectric elements in each of the piezoelectric element arrays $11_1$ to $11_N$ and $21_1$ to $21_N$ in the array direction may be determined according to the required measurement accuracy. For example, the width of the probes need not be smaller than the required measurement accuracy. When a measurement accuracy of about ±0.5 mm is required, the width of the probes is 0.5 mm or more.

Figure 5:
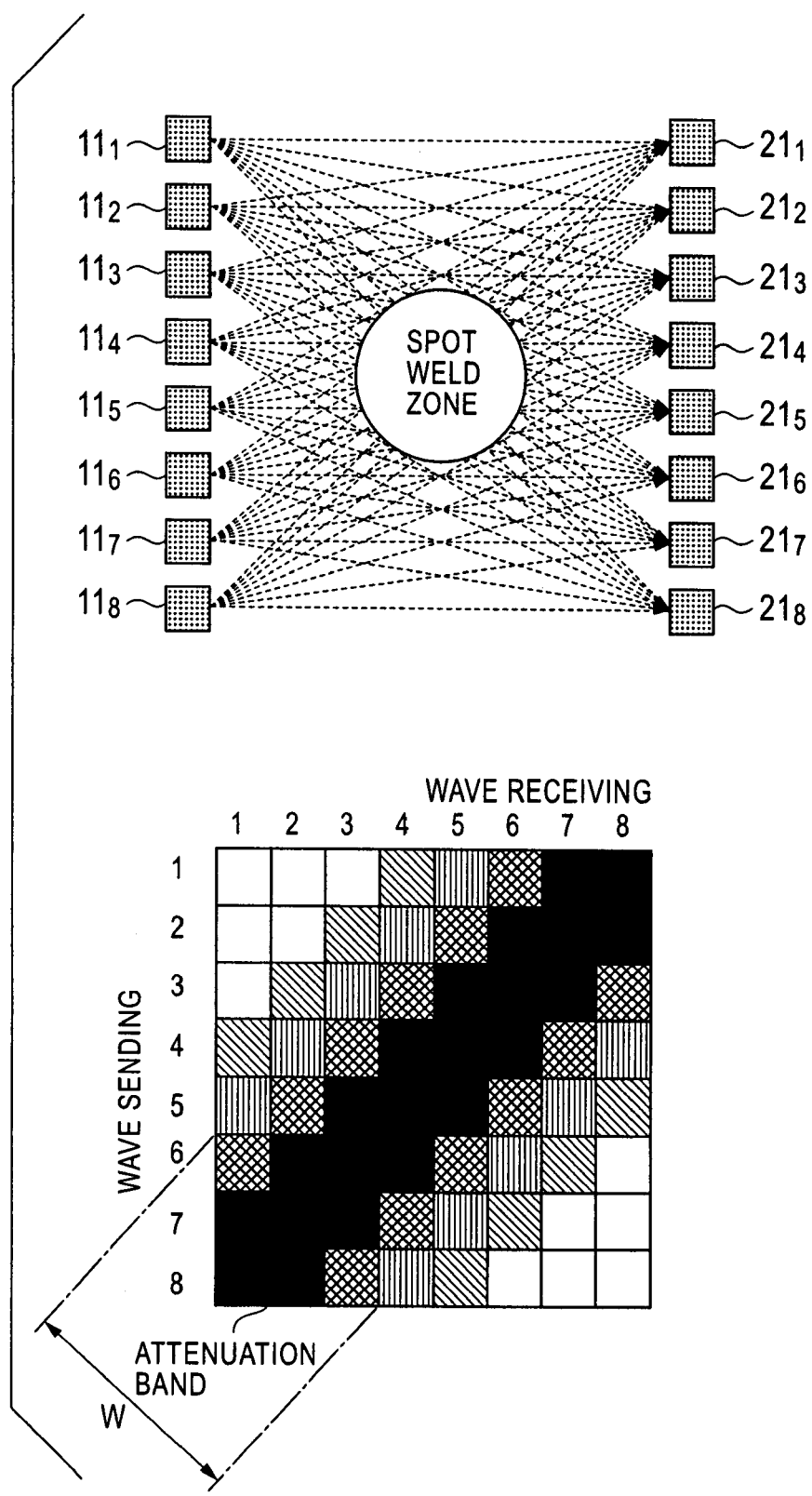
FIG. 5 is a diagram illustrating an example of a matrix display in which the relative position between ultrasonic probes and a spot weld zone is optimum.
Figure 7:
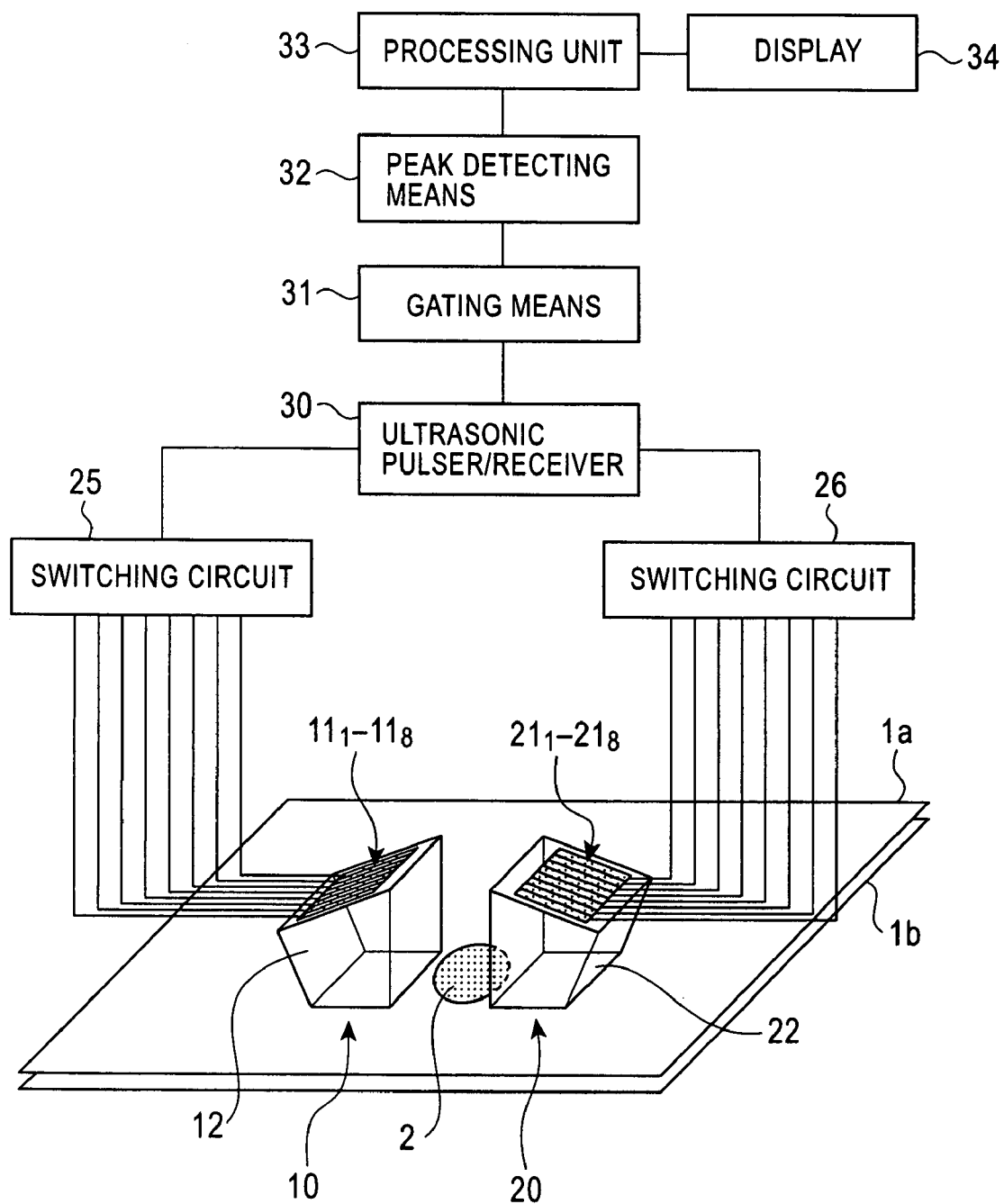
FIG. 7 is a perspective view including a block diagram showing an example of an apparatus.

FIG. 5 shows a matrix display of the results obtained by a process in which, by using an apparatus with the constitution shown in FIG. 7, the ultrasonic probes 10 and 20 opposed to each other with a spot weld zone 2 disposed therebetween are put into contact with a sample, prepared by spot welding two steel sheets having a thickness of 2.6 mm (welding conditions: passing a current of 5 kA and 15 Hz in frequency), and ultrasonic waves propagating along the 64(=8×8) paths shown in FIG. 3 are received to detect the amplitudes thereof. The ultrasonic probe 10 includes the piezoelectric element array 11 attached to the resin wedge 12 made of a polystyrol resin, the piezoelectric element array 11 including piezoelectric elements with a width of 1.5 mm in the array direction, a length of 8 mm in the direction perpendicular to the array direction, and a elements spacing of 0.1 mm in the array direction. As the piezoelectric material, a piezo-composite element with a nominal frequency of 5 MHz is used. In addition, the inclined surface of the resin wedge 12 is formed so that the angle of incidence (angle of incidence 0° equals the normal direction to the sheet) is 34.7°. The specifications of the ultrasonic probe 20 are the same as the ultrasonic probe 10. In FIG. 5, the amplitudes of the ultrasonic waves in the 64 paths are shown by hatching in 5 shading steps (practically, representation using brightness modulation or representation using gray scale is used.), and a black portion shows that the received ultrasonic wave had a low amplitude. Furthermore, in FIG. 5, numerals 1 to 8 in the longitudinal direction represent the respective piezoelectric elements $11_1$ to $11_8$ of the piezoelectric element array of the ultrasonic probe 10 used for sending ultrasonic waves, and numerals 1 to 8 in the transverse direction represent the respective piezoelectric elements $21_1$ to $21_8$ of the piezoelectric element array of the ultrasonic probe 20 used for receiving ultrasonic waves. In the matrix shown in FIG. 5, the amplitudes of received waves with the propagating paths including the weld solidified structure 2b are displayed along a diagonally right-up direction at 45°. Thereinafter, a black portion is referred to as an "attenuation band". The width W (length in the diagonally right-down direction at 45°) of the attenuation band is proportional to the size of the weld solidified structure 2b, i.e., the nugget diameter, as viewed from a direction vertical to the sheet surface. The example shown in FIG. 5 indicates that the positional relation between the ultrasonic probes 10 and 20 and the spot weld zone is optimum.

Figure 6A:
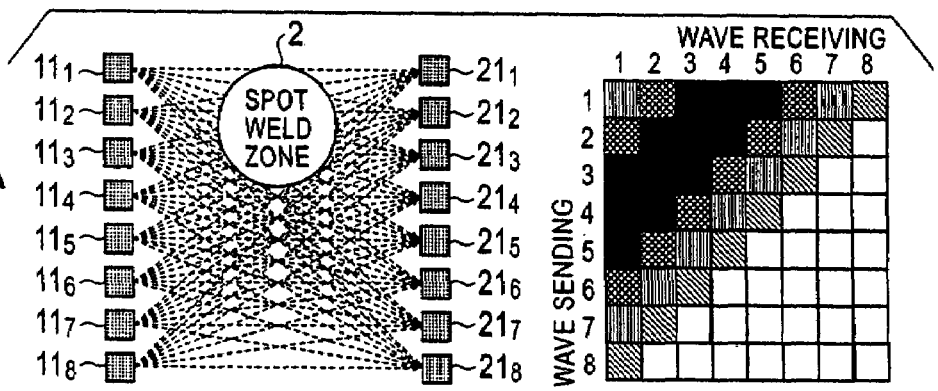
FIGS. 6A to 6D are drawings each illustrating an example of a matrix display in which the relative position between ultrasonic probes and a spot weld zone is deviated.
Figure 6B:
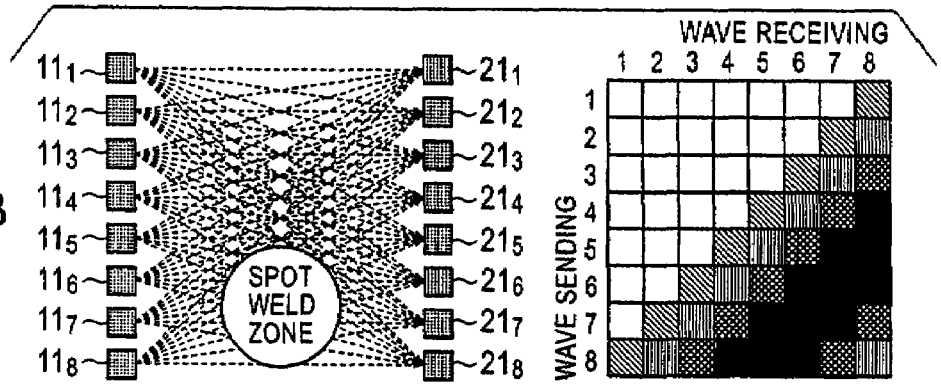
Figure 6C:
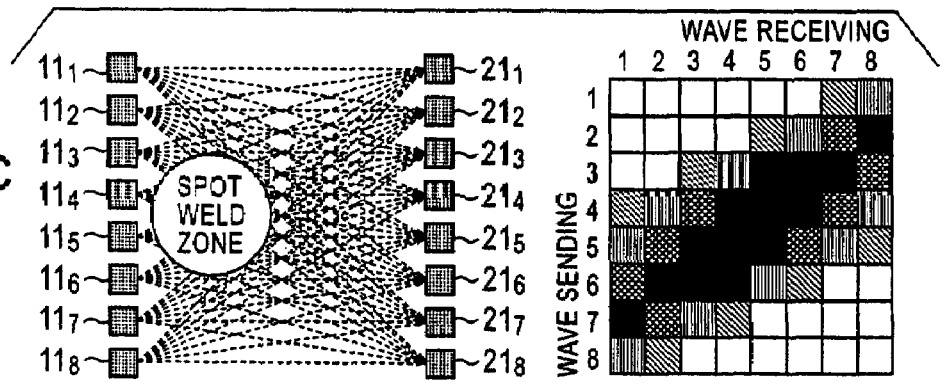
Figure 6D:
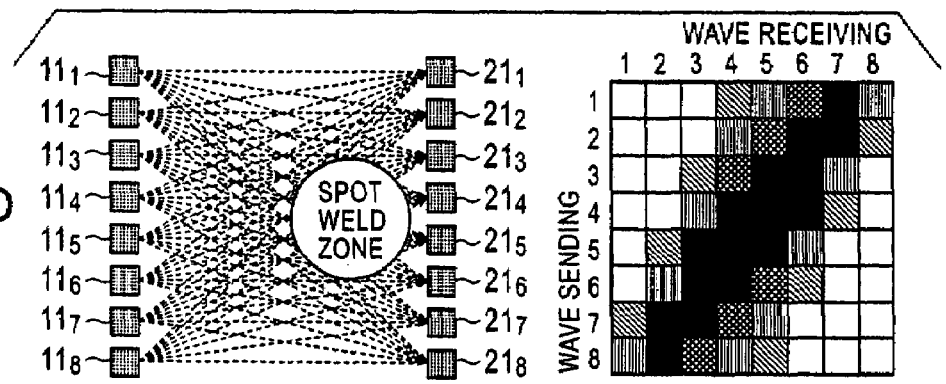

The method described above, in which the ultrasonic waves transmitted from a plurality of positions and propagating in a plurality of directions are received by the piezoelectric elements $21_1$ to $21_N$ of the ultrasonic probe 20 and the amplitudes of the received ultrasonic waves are shown in the matrix display, has the following advantage: FIGS. 6A and 6B each show the case in which the positional relation between the ultrasonic probes 10 and 20 and the spot weld zone 2 is deviated in the piezoelectric element array direction (longitudinal direction of the drawing), and FIGS. 6C and 6D each show the case in which the positional relation between the ultrasonic probes 10 and 20 and the spot weld zone 2 is deviated in the direction (lateral direction of the drawing)

perpendicular to the piezoelectric element array direction. In each of FIG. 6, planar paths of ultrasonic waves are shown by broken lines. As shown in FIGS. 6A and 6B, when the positional relation between the ultrasonic probes 10 and 20 and the spot weld zone 2 is deviated in the array direction, the attenuation band is moved to the upper left (FIG. 6A) or the lower right (FIG. 6B) in the matrix display in comparison to FIG. 5. As shown in FIGS. 6C and 6D, when the positional relation between the ultrasonic probes 10 and 20 and the spot weld zone 2 is deviated in the direction perpendicular to the piezoelectric element array direction, bright displays which show low attenuation of ultrasonic waves appear at the upper and lower ends (FIG. 6C) or the right and left ends (FIG. 6D) of the matrix display. Therefore, whether or not the positional relation between the ultrasonic probes 10 and 20 and the spot weld zone 2 is deviated can be determined from the contents of the matrix display. On the other hand, FIG. 5 shows the example in which the positional relation between the ultrasonic probes 10 and 20 and the spot weld zone 2 is optimum because the attenuation band clearly positions on a diagonal line of the matrix display.

The positional relation between the ultrasonic probes 10 and 20 and the spot weld zone 2 can be controlled by using the matrix display. Therefore, since the positional relation between the ultrasonic probes 10 and 20 and the spot weld zone 2 is always kept constant, the soundness (the presence of a nugget, nugget diameter, and the presence of weld cracks) of the spot weld zone can be evaluated with high reliability.

Furthermore, since ultrasonic waves transmitted from a plurality of positions using the piezoelectric element array $11_1$ to $11_N$ the ultrasonic probe 10 and propagating in a plurality of directions are received by the piezoelectric element array $21_1$ to $21_N$ of the ultrasonic probe 20, ultrasonic waves propagating in the paths not containing the weld solidified structure $2b$ can be received. These ultrasonic waves are shown in white in the matrix displays of FIGS. 5 and 6. By controlling the amplification gains so that the amplitudes of these ultrasonic waves get constant, changes in the amplitudes of the received ultrasonic waves caused by changes in the coupling condition between the ultrasonic probes 10 and 20 and the metal sheet ($1a$) can be compensated. Therefore, according to the present invention, it is possible to remove the influence of changes in the coupling condition between the ultrasonic probes and the metal sheet on the amplitudes of the received ultrasonic waves, thereby permitting the soundness evaluation of a spot weld zone with high reliability.

FIG. 7 shows an example of an apparatus for carrying out the method. The apparatus includes the ultrasonic probe 10 provided with the piezoelectric element array $11_1$ to $11_8$ used for transmitting ultrasonic waves, the ultrasonic probe 20 provided with the piezoelectric element array $21_1$ to $21_8$ used for receiving ultrasonic waves, an ultrasonic pulser/receiver 30 for supplying electric pulses used for transmitting ultrasonic waves from the piezoelectric elements of the piezoelectric element array $11_1$ to $11_8$ and amplifying signals of the ultrasonic waves received by the piezoelectric element array $21_1$ to $21_8$, a switching circuit 25 interposed between the ultrasonic pulser/receiver 30 and the piezoelectric element array $11_1$ to $11_8$ in order to switch the connections between the piezoelectric elements in the piezoelectric element array $11_1$ to $11_8$ and the ultrasonic pulser/receiver 30, a switching circuit 26 interposed between the ultrasonic pulser/receiver 30 and the piezoelectric element array $21_1$ to $21_8$ in order to switch the connections between the piezoelectric elements in the piezoelectric element array $21_1$ to $21_8$ and the ultrasonic pulser/receiver 30, gating means 31 for extracting the signals of the ultrasonic waves propagating along the surface of the test object among the signals amplified by the ultrasonic pulser/receiver 30, peak detecting means 32 for detecting the amplitudes of the signals extracted by the gating means, and a processing unit 33 for receiving the amplitudes of the received ultrasonic waves detected by the peak detecting means 32 to perform a matrix display of the amplitudes of the received ultrasonic waves in a display 34. The gating means 31 and the peak detecting means 32 may be substituted for a means with which the signals amplified by the ultrasonic pulser/receiver 30 are subjected to A/D conversion, and the amplitudes of the signals of the ultrasonic waves propagating along the surface of the test object are detected from the digital signals using a software.

Figure 11:
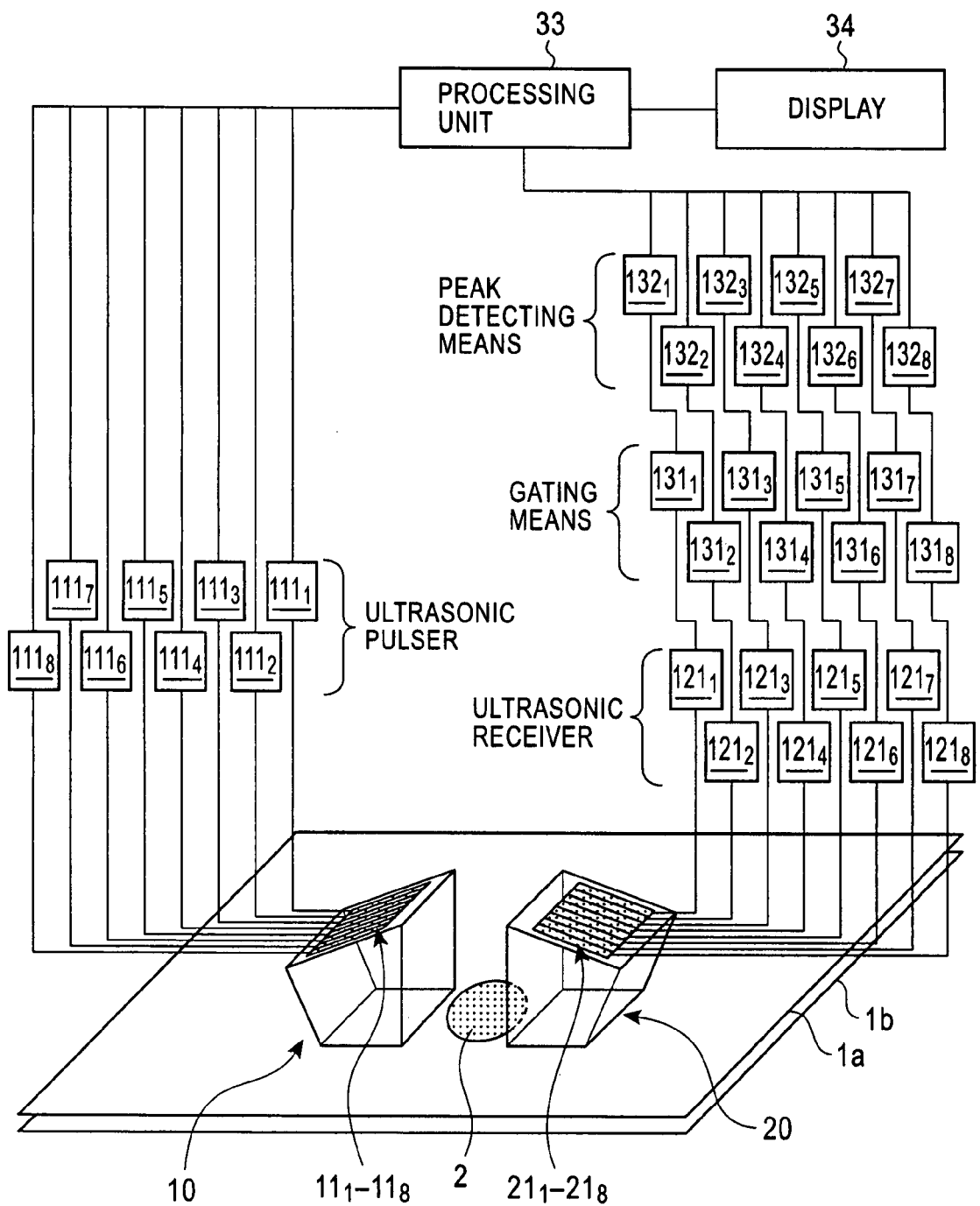
FIG. 11 is a perspective view including a block diagram showing another example of an apparatus.

FIG. 11 shows another example of an apparatus for carrying out the method. The apparatus includes the ultrasonic probe 10 provided with the piezoelectric element array $11_1$ to $11_8$ used for transmitting ultrasonic waves, the ultrasonic probe 20 provided with the piezoelectric element array $21_1$ to $21_8$ used for receiving ultrasonic waves, ultrasonic pulsers $111_1$ to $111_8$ for supplying electric pulses used for transmitting ultrasonic waves from the probes of the piezoelectric element array $11_1$ to $11_8$, ultrasonic receivers $121_1$ to $121_8$ for amplifying signals of the ultrasonic waves received by the piezoelectric element array $21_1$ to $21_8$, gating means $131_1$ to $131_8$ for extracting the signals of the ultrasonic waves propagating along the surface of the test object among the signals amplified by the ultrasonic receivers $121_1$ to $121_8$, peak detecting means $132_1$ to $132_8$ for detecting the amplitudes of the signals extracted by the gating means, and a processing unit 33 for receiving the amplitudes of the received ultrasonic waves detected by the peak detecting means $132_1$ to $132_8$ to perform a matrix display of the amplitudes of the received ultrasonic waves in a display 34. The gating means $131_1$ to $131_8$ and the peak detecting means $132_1$ to $132_8$ may be substituted for a means with which the signals amplified by the ultrasonic receivers $121_1$ to $121_8$ are subjected to A/D conversion, and the amplitudes of the signals of the ultrasonic waves propagating along the surface of the test object are detected from the digital signals using a software.

Figure 12:
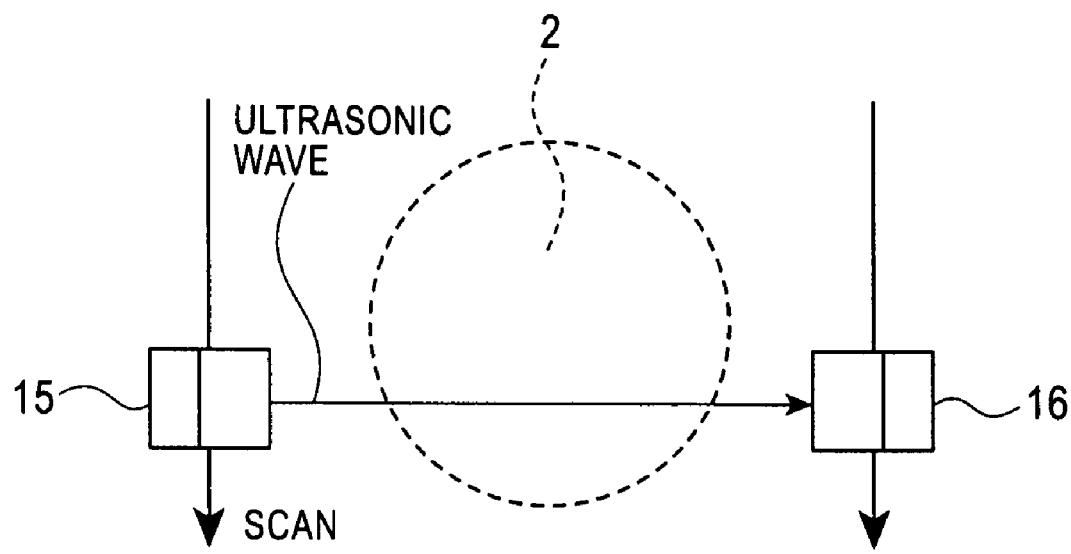
FIG. 12 is a plan view showing a constitution according to another embodiment.

In this embodiment, ultrasonic probes each provided with a piezoelectric element array are used on both the sending side and the receiving side, and thus the configuration is simplified. However, a plurality of probes may be arranged in parallel on one or both of the sending side and the receiving side, or an ultrasonic probe 15 for transmitting waves and an ultrasonic probe 18 for receiving waves each including a single probe may be scanned opposite to each other as shown in FIG. 12.

EXAMPLES

Figure 8:
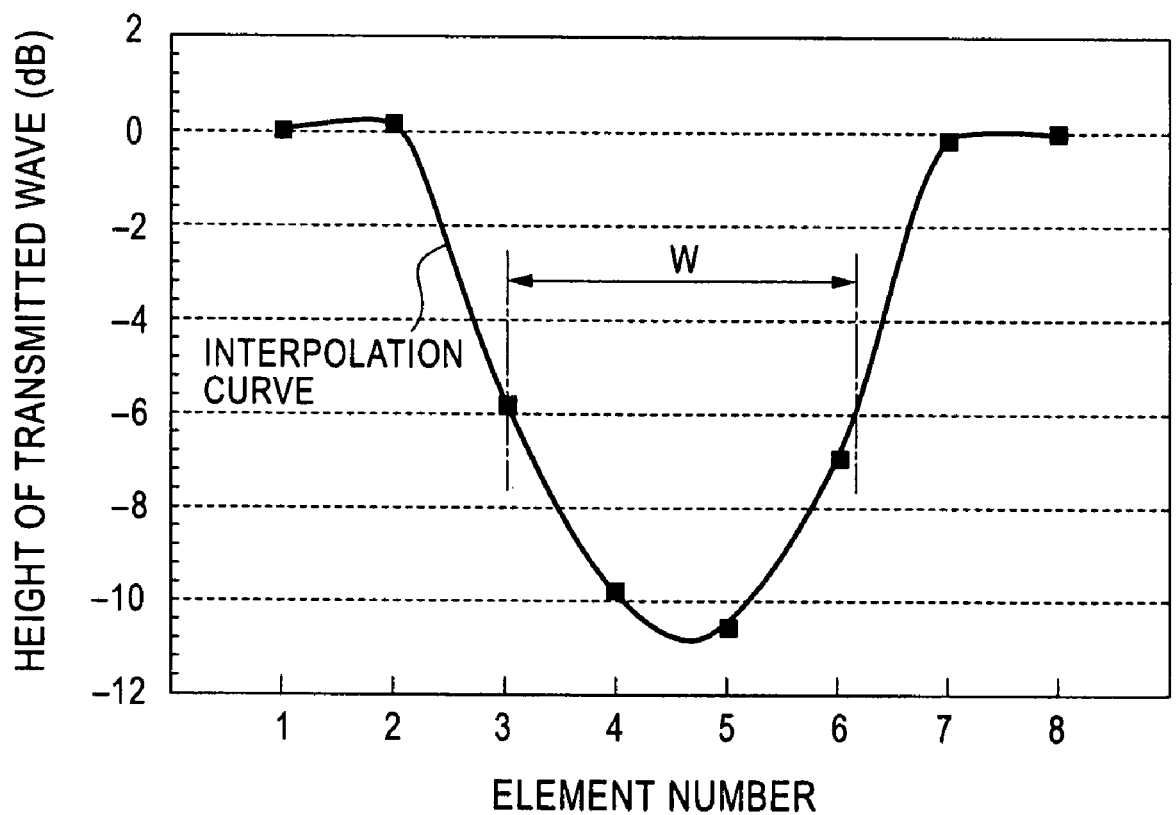
FIG. 8 is a graph showing an interpolation curve of amplitudes of received ultrasonic waves.

A spot weld zone 2 was measured using the apparatus shown in FIG. 7 in which the wedge materials 12 and 22 of the ultrasonic probes 10 and 20 were made of polystyrol, the piezoelectric element arrays $11_1$ to $11_8$ and $21_1$ and $21_8$ each included piezo-composite elements having a nominal frequency of 5 MHz, a width of 1.5 mm in the array direction, a length of 8 mm in the direction perpendicular to the array direction, and a elements spacing of 0.1 mm in the array direction, and the angle of incidence onto the surface of the upper sheet $1a$ was 34.7°. In addition, glycerin paste was interposed as a coupling medium between each of the ultrasonic probes 10 and 20 and the upper sheet $1a$. As measurement objects, 30 samples each prepared by spot welding (welding condition: passing a current of 2 to 10 kA and 15 Hz in frequency) of two steel sheets having a thickness of 2.6 mm were used. In this measurement, the relative position between the ultrasonic probes 10 and 20 and the spot weld zone 2 was controlled so that the centerline of the attenuation band coincided a right-up diagonal in a matrix display of the amplitudes of the received ultrasonic waves, as shown in FIG. 5. As shown in FIG. 8, in the measurement of the width W of the attenuation band, an amplitude profile (height of transmitted wave) of the received ultrasonic waves in the array direction was determined by interpolation using the amplitudes of the ultrasonic waves transmitted by the piezoelectric element $11n$ of the piezoelectric element array and then received by the piezoelectric element $21n$ of the piezoelectric element array ($n=1, 2, \ldots, 8$), and the width of a portion where the amplitude profile was lower than a predetermined threshold value was determined. The width W of the attenuation band was regarded as the nugget diameter. The threshold value was determined as follows: As a result of comparison between the amplitude profile and the results of microscopic observation of a sectioned surface (referred to as a "section test") using several samples, it was found that by setting the threshold value at about −6 dB for the amplitudes of ultrasonic waves propagating along the surface of the test object in the propagation paths not including the spot weld zone, the nugget diameter determined by microscopic examination coincides with the nugget diameter determined according to this disclosure. Therefore, the threshold value was determined to −6 dB. The threshold value (−6 dB) is an example, and practically, the threshold value is preferably determined on the basis of experimental values for each measurement object.

Figure 9A:
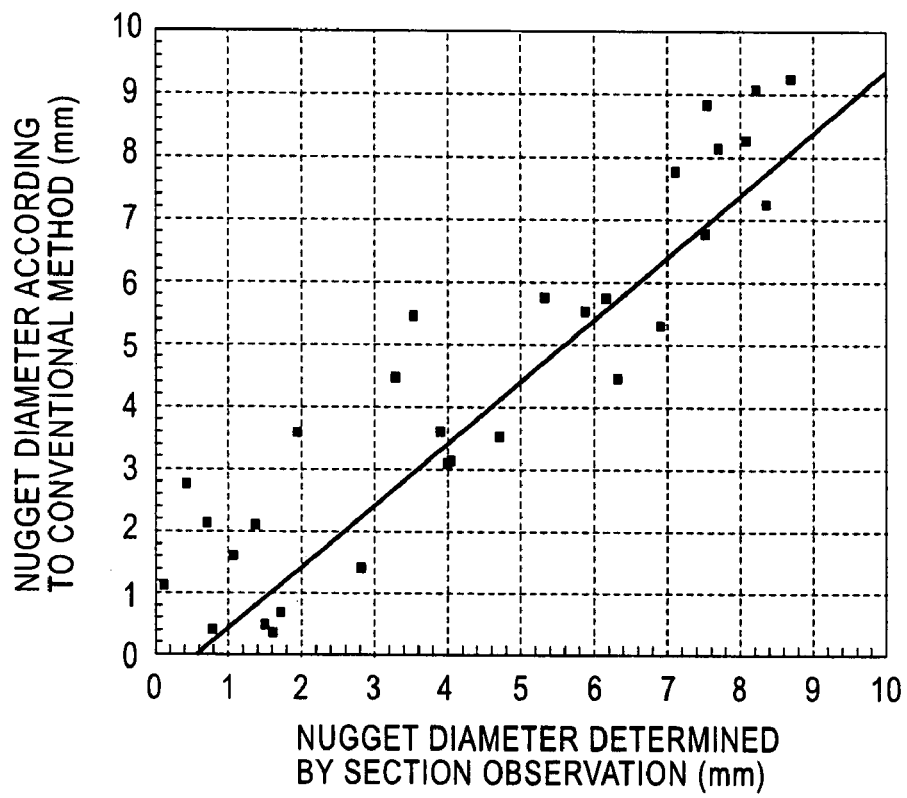
FIGS. 9A and 9B are graphs showing comparison of accuracy between the measurement results obtained by a conventional method and my method.
Figure 9B:
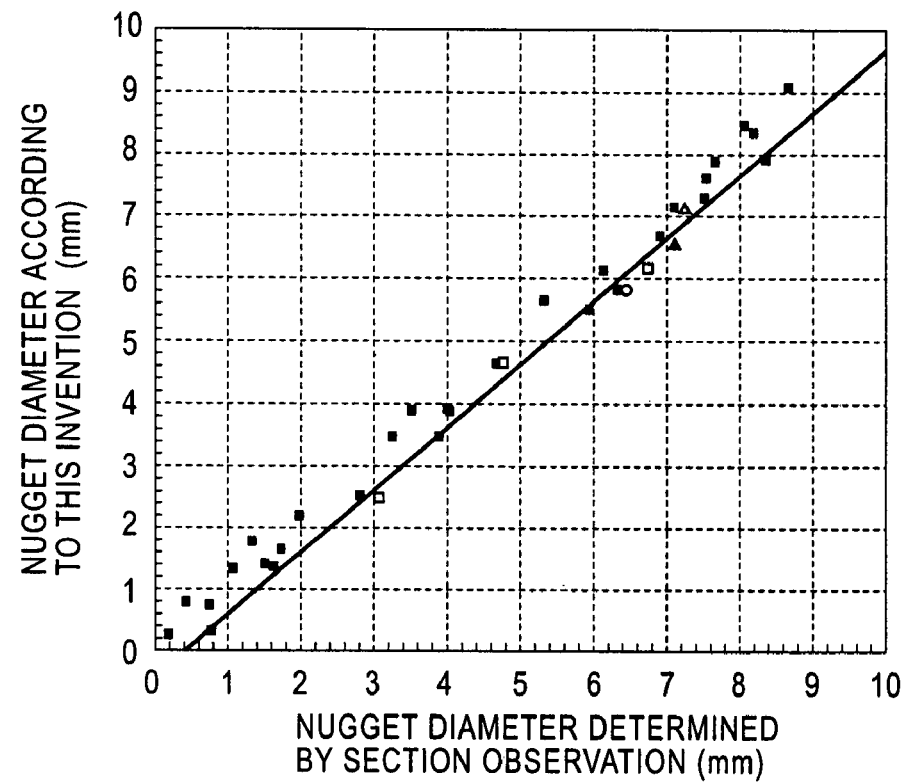
Figure 10:
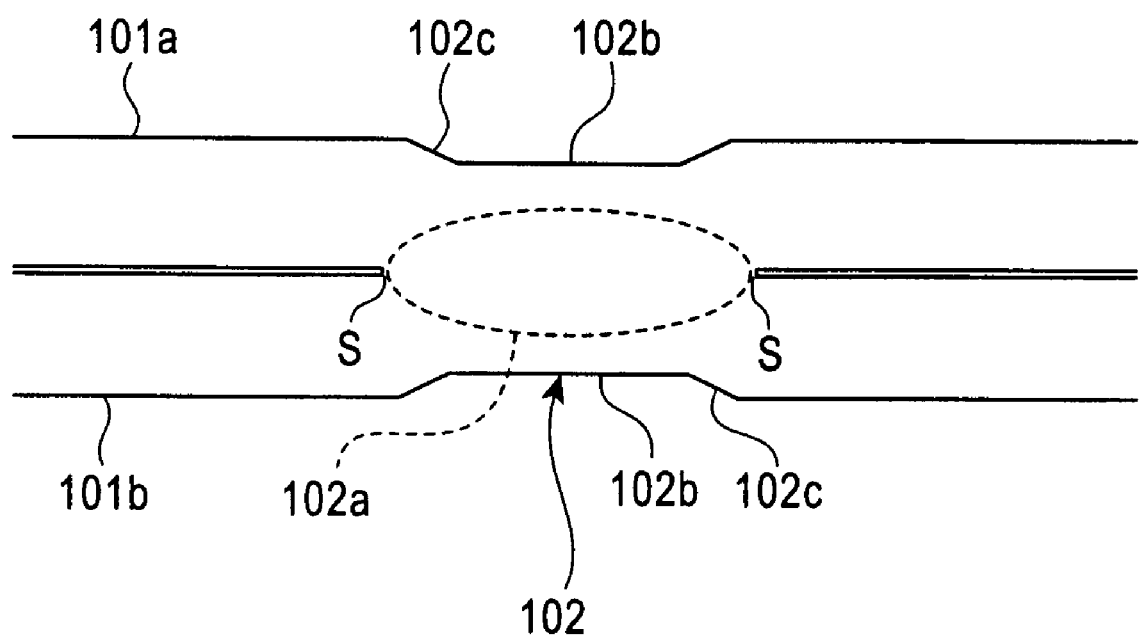
FIG. 10 is a sectional view for explaining a spot weld zone.

For the purpose of comparison to the prior art, measurement was performed using the above-described measurement method and the method disclosed in Japanese Unexamined Patent Application Publication No. 2004-163210 under the condition in which the measurement time was limited within 5 seconds after an ultrasonic probe (the Lamb wave probe disclosed in Japanese Unexamined Patent Application Publication No. 2004-163210 is also referred to as an "ultrasonic probe") was brought into contact with a sample. In the measurement, as for the method disclosed in Japanese Unexamined Patent Application Publication No. 2004-163210, an ultrasonic probe having the specifications including a nominal frequency of 5 MHz, a probe size of 10×10 mm, a wedge material composed of an acrylic resin, and an angle of 65.9° of incidence onto a sample from a wedge was used. In FIG. 9B, the results of measurement using the apparatus shown in FIG. 7 (according to the present invention) are shown by plots of ■. FIG. 9A shows the results of measurement by the method disclosed in Japanese Unexamined Patent Application Publication No. 2004-163210. Each of FIGS. 9A and 9B is a scatter graph in which the nugget diameters determined by a section test (also referred to as "section microscopic examination" in which an etched section is observed through a microscope) are shown as abscissa, and the nugget diameters determined by each of the methods are shown as ordinate. Plots of □, Δ, ▲, and ○ in FIG. 9B will be described below. In the method disclosed in Japanese Unexamined Patent Application Publication No. 2004-163210, the nugget diameter is underestimated due to the fact that the ultrasonic probes cannot be aligned with the weld solidified structure within a short time, and the nugget diameter is overestimated due to the fact that the coupling condition between the ultrasonic probes and the sample is not sufficiently stabilized within a short time and the fact that there is no means for compensating a change in the coupling condition. On the other hand, as a result of measurement according to the present invention, all measured values fall in the range of ±0.5 mm, and it is thus found that measurement results with high reliability can be rapidly obtained. This is due to the fact that the alignment between the ultrasonic probes and the spot weld zone (weld solidified structure) can be easily performed by a matrix display of amplitudes of received ultrasonic waves, and sensitivity is controlled so that the amplitudes of the received ultrasonic waves propagating along the paths not containing the weld solidified structure is constant, thereby compensating a change in amplitudes of the received ultrasonic waves with a change in the coupling condition between the ultrasonic probes and the metal sheet.

The nugget diameter can also be determined using the method disclosed in Japanese Unexamined Patent Application Publication No. 2004-163210 in which the ratios of the minimum amplitude of received ultrasonic waves to the amplitudes of received ultrasonic waves with the paths not containing the weld solidified structure are determined using the amplitude profile of received ultrasonic waves in the array direction shown in FIG. 8.

Figure 13:
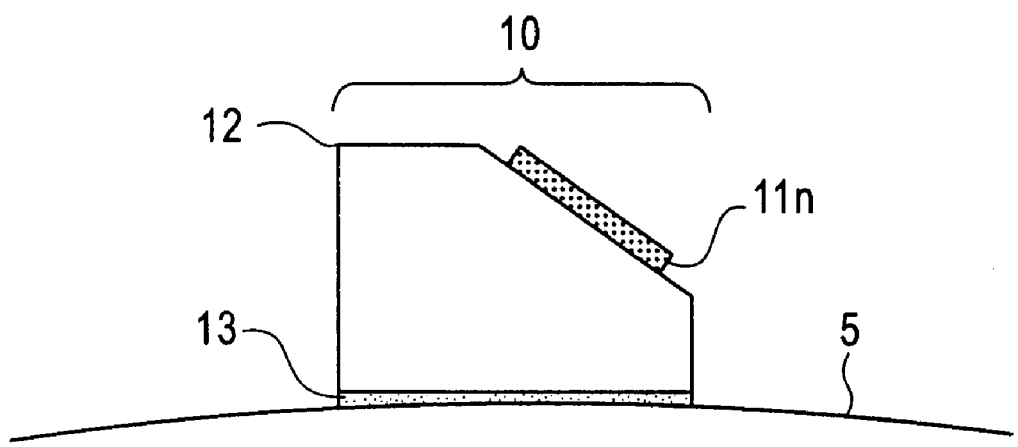
FIG. 13 is a sectional view showing the measurement of a curved surface through a flexible member.

FIG. 13 is a sectional view showing the state in which the ultrasonic probe 10 with a contact surface to which a silicone rubber film of 0.5 mm in thickness is attached is pressed on a gently curved surface 5. The same silicone rubber is attached to the ultrasonic probe 20. These ultrasonic probes 10 and 20 were used for measuring a nugget diameter of a spot weld sample made by spot welding (welding conditions: passing a current of 4 to 8 kA and 15 Hz in frequency) of two steel sheets having a thickness of 2.6 mm and a radius of curvature of 100 mm, and the measured nugget diameters were compared with the nugget diameters determined by the section test. The results are shown by □ plots in FIG. 9B. Even for a spot weld zone of metal sheets with curvature, a nugget diameter can be correctly measured using the method and apparatus of this disclosure.

In FIG. 9B, Δ plots show the results of comparison between the nugget diameters measured using the apparatus shown in FIG. 7 (inventive example) and the nugget diameters measured by the section test using samples formed as a measurement object by spot welding (welding conditions: passing a current of 10 kA and 26 Hz in frequency) of three steel sheets having thicknesses of 0.8 mm, 2.0 mm, and 2.6 mm. In FIG. 9B, ▲ plots show the results of comparison between the nugget diameters measured using the apparatus shown in FIG. 7 (inventive example) and the nugget diameters measured by the section test using samples made as a measurement object by spot welding (welding conditions: passing a current of 11 kA and 24 Hz in frequency) of four steel sheets having thicknesses of 0.8 mm, 0.8 mm, 1.2 mm, and 2.3 mm. In FIG. 9B, ○ plots show the results of comparison between the nugget diameters measured using the apparatus shown in FIG. 7 (inventive example) and the nugget diameters measured by the section test using samples made as a measurement object by spot welding (welding conditions: passing a current of 12 kA and 22 Hz in frequency) of five steel sheets having thicknesses of 0.8 mm, 0.8 mm, 0.8 mm, 1.2 mm, and 1.6 mm. These results show that even when the number of metal sheets to be welded is 3 to 5, the nugget diameter can be correctly measured using the method and apparatus of this disclosure.

Figure 14A:
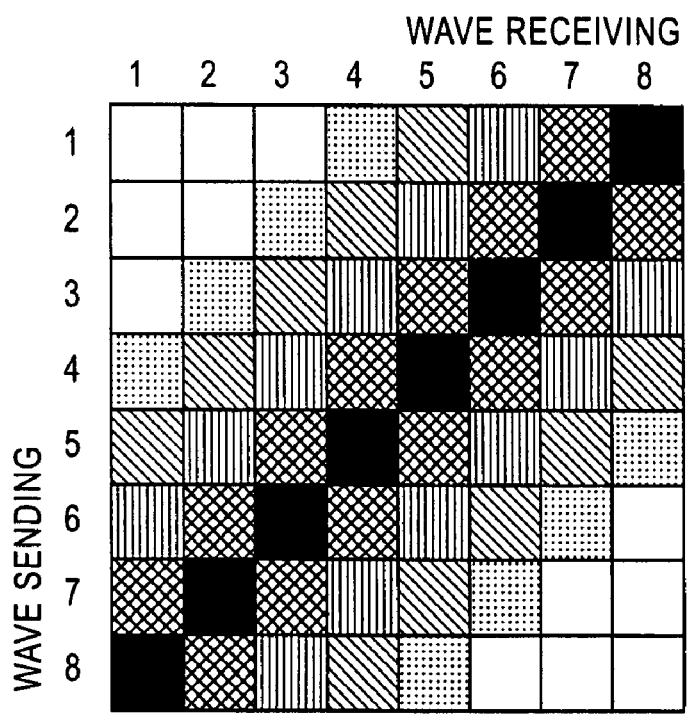
FIGS. 14A and 14B are diagrams showing a comparison between an example of a matrix display having a crack and a matrix display without a crack.
Figure 14B:
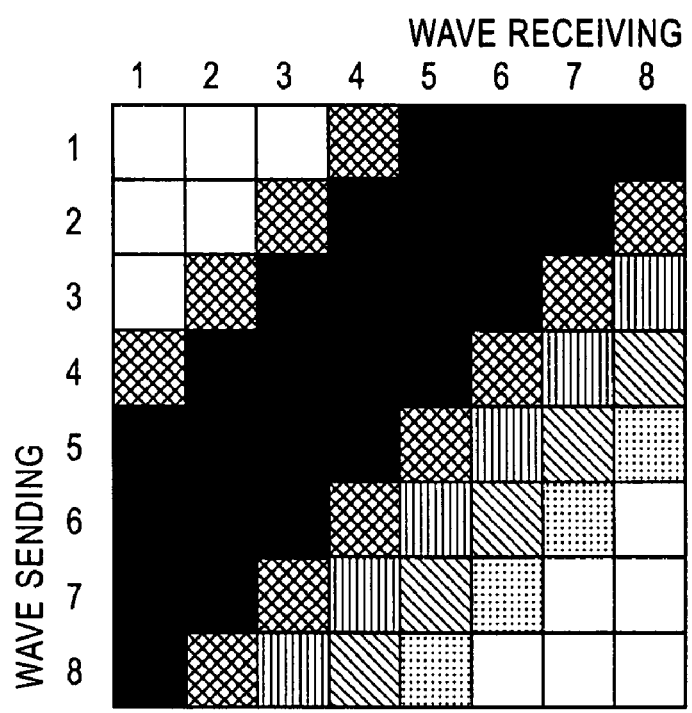

The evaluation of soundness of a spot welt zone is not limited to the measurement of only the nugget diameter. For example, FIG. 14A shows a matrix display in measurement of a spot weld zone with a weld crack using the apparatus shown in FIG. 7. For comparison, FIG. 14B shows a matrix display in measurement of a spot weld zone with no weld crack made under equivalent welding conditions. Since the density of the attenuation band or brightness in the pattern of a matrix display significantly changes asymmetrically with respect to a right-up diagonal due to the presence of a welding crack, a welding crack can be detected by observing a matrix display.

INDUSTRIAL APPLICABILITY

A spot weld zone can be precisely evaluated by a nondestructive method without being influenced by an inclined surface formed around a dimple formed in the spot weld zone. In addition, even in measurement in which the measurement time is limited to a short time, the soundness of a spot weld zone can be evaluated with high reliability without being influenced by a positional deviation between an ultrasonic probe and the spot weld zone and the coupling condition between an ultrasonic probe and a metal sheet.

The invention claimed is:

1. An ultrasonic method for evaluating a spot weld zone formed by welding a plurality of stacked metal sheets, wherein an ultrasonic wave propagating in a sectional plane which has one axis parallel to the surface of the metal sheets or the spot weld zone and has another axis parallel to the thickness direction is referred to as an ultrasonic wave propagating along the surface of a test object, comprising:

transmitting ultrasonic waves propagating along the surface of the test object in a plurality of directions from a plurality of wave sending positions outside the spot weld zone in the metal sheets, and receiving ultrasonic waves propagating along the surface of the test object with propagation paths not including the spot weld zone and ultrasonic waves propagating along the surface of the test object with propagation paths including the spot weld zone at a plurality of wave receiving positions outside the spot weld zone to evaluate soundness of the spot weld zone on the basis of the ultrasonic waves received at the plurality of wave receiving positions.

2. The method according to claim 1, wherein the amplitudes of the received ultrasonic waves are detected to measure the diameter of a nugget of the spot weld zone.

3. An ultrasonic apparatus for evaluating a spot weld zone formed by welding a plurality of stacked metal sheets, wherein an ultrasonic wave propagating in a sectional plane which has one axis parallel to the surface of the metal sheets or the spot weld zone and has another axis parallel to the thickness direction is referred to as an ultrasonic wave propagating along the surface of a test object, comprising:

means for transmitting ultrasonic waves propagating along the surface of a test object in a plurality of directions from a plurality of wave sending positions outside the spot weld zone in the metal sheets, and means for receiving ultrasonic waves propagating along the surface of the test object with propagation paths not including the spot weld zone and ultrasonic waves propagating along the surface of the test object with propagation paths including the spot weld zone at a plurality of wave receiving positions outside the spot weld zone to evaluate soundness of the spot weld zone on the basis of the ultrasonic waves received at the plurality of wave receiving positions.

4. The apparatus according to claim 3, wherein the amplitudes of the received ultrasonic waves are detected to measure the diameter of a nugget of the spot weld zone.

5. The apparatus according to claim 4, wherein the amplification gains of signals of the received ultrasonic waves are controlled on the basis of the amplitudes of the ultrasonic waves propagating along the surface of the test object with the propagation paths not including the spot weld zone.

6. The apparatus according to claim 4, wherein the amplitudes of the signals transmitted from the respective wave sending positions and received at the respective wave receiving positions are displayed in a matrix.

7. The apparatus according to claim 6, wherein the positional relation between the spot weld zone and the means for transmitting ultrasonic waves and the means for receiving ultrasonic waves is controlled on the basis of the display results of display means.

8. The apparatus according to claim 6, wherein the means for transmitting ultrasonic waves propagating along the surface of the test object in a plurality of directions from a plurality of wave sending positions includes an ultrasonic probe provided with a piezoelectric element array.

9. The apparatus according to claim 6, wherein the means for receiving ultrasonic waves at a plurality of wave receiving positions includes an ultrasonic probe provided with a piezoelectric element array.

10. The apparatus according to claim 8, wherein a flexibly deformable member is attached to the contact surface of the ultrasonic probe provided with the piezoelectric element array.

11. The apparatus according to claim 3, wherein the amplitudes of the signals transmitted from the respective wave sending positions and received at the respective wave receiving positions are displayed in a matrix.

12. The apparatus according to claim 11, wherein the positional relation between the spot weld zone and the means for transmitting ultrasonic waves and the means for receiving ultrasonic waves is controlled on the basis of the display results of display means.

13. The apparatus according to claim 3, wherein the means for transmitting ultrasonic waves propagating along the surface of the test object in a plurality of directions from a plurality of wave sending positions includes an ultrasonic probe provided with a piezoelectric element array.

14. The apparatus according to claim 13, wherein a flexibly deformable member is attached to the contact surface of the ultrasonic probe provided with the piezoelectric element array.

15. The apparatus according to claim 3, wherein the means for receiving ultrasonic waves at a plurality of wave receiving positions includes an ultrasonic probe provided with a piezoelectric element array.

* * * * *

UNITED STATES PATENT AND TRADEMARK OFFICE
CERTIFICATE OF CORRECTION

PATENT NO. : 7,698,944 B2
APPLICATION NO. : 11/661741
DATED : April 20, 2010
INVENTOR(S) : Hajime Takada It is certified that error appears in the above-identified patent and that said Letters Patent is hereby corrected as shown below:

In Column 5
In the "REFERENCE NUMERALS", at line 37, on the following line, after "12, 22 resin wedge" please insert the following:

| | |
|---|---|
| --13 | silicone rubber |
| 15 | ultrasonic probe for transmitting waves |
| 16 | ultrasonic probe for receiving waves |
| 25, 26 | switching circuit |
| 30 | ultrasonic pulser/receiver |
| 31, 131 | gating means |
| 32, 132 | peak detecting means |
| 33 | processing unit |
| 34 | display |
| 111 | ultrasonic transmitter |
| 121 | ultrasonic receiver |

Detailed Description
A representative embodiment of my disclosure will be described in detail below with reference to the drawings.
The evaluation of a spot weld zone formed by bonding two metal sheets will be described as an example. Of the two sheets, a sheet on the upper side is referred to as an "upper sheet", and a sheet on the lower side is referred to as a "lower sheet". As shown in Fig. 1, an ultrasonic probe 10 provided with a piezoelectric element array 11 and an ultrasonic probe 20 provided with a piezoelectric element array 21 are brought into contact with the upper sheet 1a to be opposed to each other with a spot weld zone 2 disposed therebetween. A proper coupling medium is interposed between the upper sheet 1a and each of the ultrasonic probes 10 and 20.--

In column 6
At lines 5 and 6, please delete "For example, as the coupling medium, glycerin, glycerin paste, machine oil, alcohol, or water can be used.", and Signed and Sealed this
Twenty-sixth Day of April, 2011

David J. Kappos
*Director of the United States Patent and Trademark Office*

At lines 7 through 38 please delete the entire paragraph beginning with "In addition".